(12) United States Patent
Dingwell et al.

(10) Patent No.: US 6,250,166 B1
(45) Date of Patent: Jun. 26, 2001

(54) SIMULATED DOVETAIL TESTING

(75) Inventors: William T. Dingwell, West Chester; Andrew J. Lammas, Maineville, both of OH (US)

(73) Assignee: General Electric Company, Cincinnati, OH (US)

( * ) Notice: Subject to any disclaimer, the term of this patent is extended or adjusted under 35 U.S.C. 154(b) by 0 days.

(21) Appl. No.: 09/327,276

(22) Filed: Jun. 4, 1999

(51) Int. Cl.[7] .................................. G01N 3/02; G01N 3/32
(52) U.S. Cl. ...................................... 73/810; 73/808
(58) Field of Search ..................... 73/865.9, 808, 73/810, 821, 813, 811, 845, 815, 804

(56) References Cited

U.S. PATENT DOCUMENTS

| | | | |
|---|---|---|---|
| 5,046,398 | * 9/1991 | Baumel | 73/810 |
| 5,601,933 | * 2/1997 | Hajmrle et al. | 428/660 |
| 5,937,530 | 8/1999 | Messon | 73/865.5 X |
| 6,033,185 | 3/2000 | Lemmes et al. | 416/193 A |
| 6,035,730 | 3/2000 | Kewese | 73/865.9 |

* cited by examiner

*Primary Examiner*—Thomas P. Noland
(74) *Attorney, Agent, or Firm*—Andrew C. Hess; Gerry S. Gressel

(57) ABSTRACT

A dovetail of a rotor blade is mounted in a complementary slot in a rotor disk. Life of the dovetail is simulated by providing a specimen dovetail mounted in a complementary slot in a fixture. Relative stiffness of the specimen dovetail and fixture are tailored to simulate the loading profile between the blade dovetail and rotor disk. Load is cycled between the specimen dovetail and fixture for determining life of the dovetail.

20 Claims, 5 Drawing Sheets

SIMULATED DOVETAIL TESTING

BACKGROUND OF THE INVENTION

The present invention relates generally to gas turbine engines, and, more specifically, to endurance testing of rotor blades therein.

In a gas turbine engine, air is pressurized in a compressor and mixed with fuel and ignited in a combustor for generating hot combustion gases. The gases flow downstream through turbine stages which extract energy therefrom for powering the compressor and producing useful work, such as powering a fan for propelling an aircraft in flight, for example.

In the compressor and turbines, stationary stator vanes direct air or gas between corresponding rotor blades for compressing the air or extracting energy from the combustion gases. Each rotor blade has an airfoil with an integral dovetail configured for being radially retained in a corresponding dovetail slot in the perimeter of a rotor disk. The dovetails may either be axial-entry or circumferential-entry, and are mounted in corresponding axial or circumferential dovetail slots in the perimeter of the corresponding rotor disks.

The blade dovetails may have various configurations due to the different blade size and function of the compressor and turbines. A typical dovetail includes a pair of lobes extending radially inwardly from a shank or neck of minimum cross section. The corresponding rotor disk includes a complementary dovetail slot defined between a pair of radially outwardly extending tangs. The dovetail lobes include radially outwardly facing contact or pressure faces which engage corresponding radially inwardly facing contact or pressure faces of the tangs.

During rotation of the blades in operation, centrifugal force or load is developed in each blade and is carried radially inwardly through the dovetails and reacted by the rotor disk. The centrifugal loads effect a nominal crush load over the corresponding pressure faces which causes a crush stress represented by the load divided by the contacting surface area of the pressure faces.

The rotor blades are also subject to aerodynamic loading by the air or combustion gases which flow over the corresponding airfoils during operation. For example, a multistage axial compressor includes respective rows of compressor blades decreasing in size for increasing pressure of the air in turn from stage to stage. Accordingly, the air pressure developed aft of the blade trailing edge is greater than the pressure forward of the blade leading edge, and effects a corresponding bending moment which is reacted by the dovetail lobes.

Accordingly, blade dovetails are designed in cooperation with their respective rotor disks for accommodating the various centrifugal and aerodynamic loads occurring during operation. Additionally, dovetail design must also accommodate thermal stresses due to the elevated temperatures experienced in the compressor as it pressurizes the air, as well as in the turbines heated by the hot combustion gases.

Compressor blades are typically designed for having an infinite life without undesirable cracking therein. For example, one type of large turbofan gas turbine engine has enjoyed many years of successful commercial use in this country, as well as abroad. The engine includes a high pressure compressor having several rows of circumferential entry compressor blades made of titanium.

The engine undergoes periodic field inspection of its various parts which has recently revealed undesirable cracking in some of the compressor blade dovetails having enjoyed high time operation with a substantial number of cycles and engine hours. The discovery of even a single crack requires the replacement of the entire row of compressor blades for ensuring optimum performance. Such cracking ends the useful life of the blades, which therefore fail to achieve the desired infinite life.

Accordingly, improved blade dovetail designs are being developed for addressing this high time dovetail cracking occurrence for further improving the engine design and reducing maintenance costs.

Modern three dimensional (3D) finite element analysis has been used to discover the source of high time compressor blade dovetail cracking. The dovetail neck, having minimum cross sectional area between the dovetail lobes, is initially the life limiting region of the dovetail having maximum local stress. The dovetail neck is therefore typically designed for suitably low stress to achieve infinite life.

However, analysis has uncovered that frictional shear forces develop during operation between the pressure faces and increase in magnitude as the blade accumulates cycles of operation. The friction force changes the loading profile experienced by the pressure faces and creates locally maximum contact stress at the two opposite edges of contact of each pressure face.

Accordingly the radially outer edge of contact located near the dovetail neck eventually experiences higher local stress than the neck itself in high time compressor blades. In particular, the forward lobe of a circumferential entry compressor blade dovetail experiences higher edge of contact stress than the aft lobe. And, the high-stress edges of contact provide crack initiation sites which may lead to premature dovetail failure.

The development of improved blade dovetails accommodating edge of contact stress necessarily requires suitable testing thereof for evaluating performance of the design. One conventional type of testing utilizes a whirligig in which an actual compressor rotor or spool is rotated to speed. The rotor includes an actual dovetail slot, such as a circumferential slot, in which is mounted an actual compressor blade for testing. Although the rotor may be operated at corresponding rotational speed to simulate actual operation in an engine, aerodynamic loading of the compressor blades is not included in the test. Such testing therefore has limited capability, and typically requires weeks or months of blade cycling to achieve sufficient high time cycles of operation.

Another conventional dovetail test includes an apparatus for pulling an individual compressor blade in tension in its corresponding dovetail slot. Tension loads are suitably cycled for achieving centrifugal loads and stress comparable to those obtained during actual rotary operation in an engine. However, the blade component pull test also fails to introduce aerodynamic loading. And, the dovetail slot is typically simulated using only a portion of an actual rotor disk which permits undesirable bending of the disk tangs leading to separation of the pressure faces in part near the outer edges of contact thusly changing the loading profile.

Although the whirligig testing and component pull testing may be effectively used for simulating dovetail neck stresses during operation, they are ineffective for simulating the complex loading profile at the pressure faces, and in particular at the edges of contact.

Accordingly, it is desired to provide an improved apparatus and method for more accurately simulating dovetail loading in cycle testing.

BRIEF SUMMARY OF THE INVENTION

A dovetail of a rotor blade is mounted in a complementary slot in a rotor disk. Life of the dovetail is simulated by providing a specimen dovetail mounted in a complementary slot in a fixture. Relative stiffness of the specimen dovetail and fixture are tailored to simulate the loading profile between the blade dovetail and rotor disk. Load is cycled between the specimen dovetail and fixture for determining life of the dovetail.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
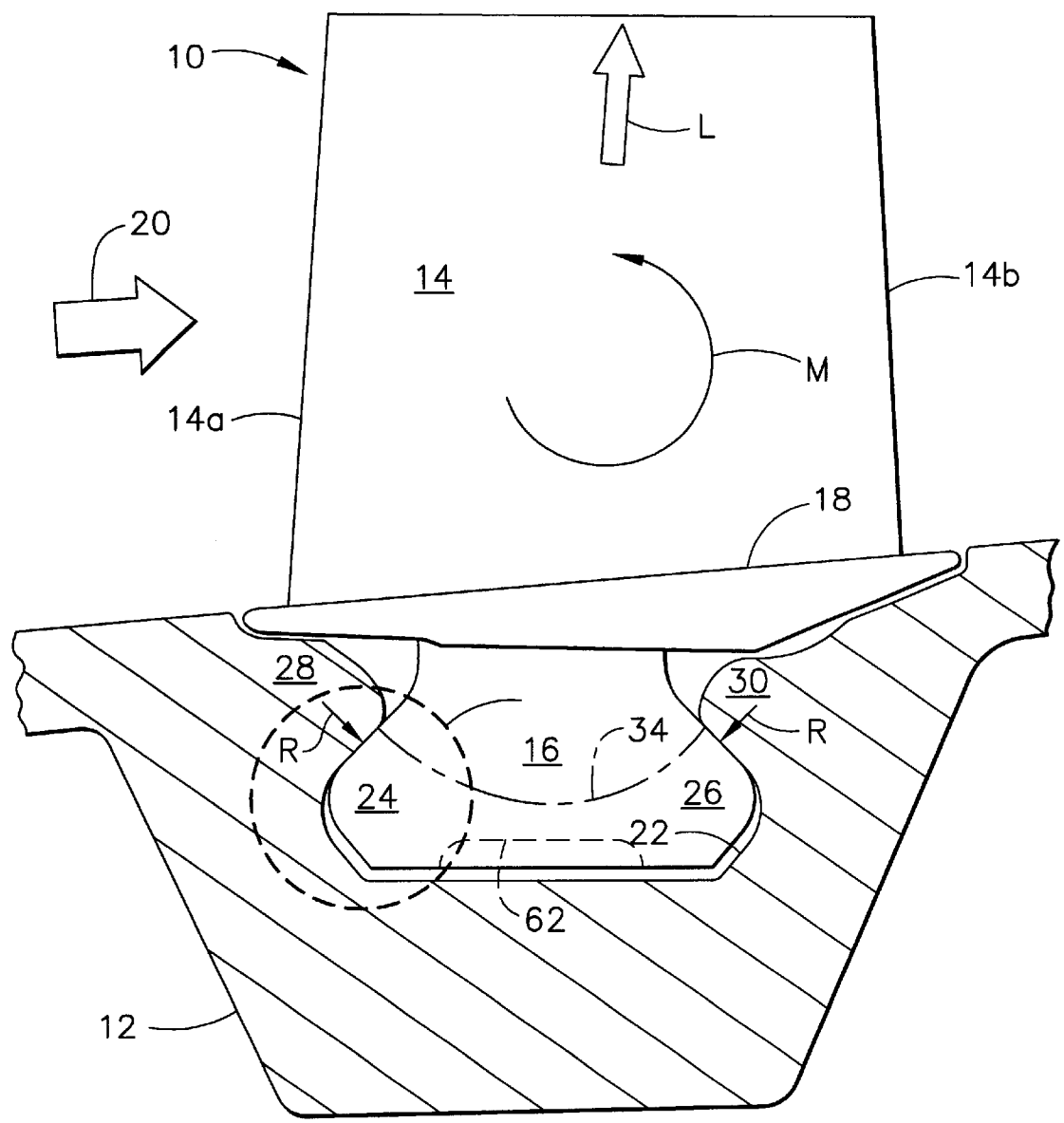
FIG. 1 is an elevational, partly sectional view of an exemplary compressor rotor blade having a circumferential-entry dovetail mounted in a complementary slot in the perimeter of a rotor disk.

Illustrated in FIG. 1 is one of several exemplary compressor rotor blades 10 mounted to the perimeter of a supporting rotor disk 12 in a conventional manner. For example, the compressor blade and disk are representative of one or more stages of a multi-stage axial high pressure compressor of an aircraft turbofan gas turbine engine in a preferred embodiment.

The blade 10 includes an airfoil 14 integrally formed with a circumferential-entry dovetail 16 with an intervening integral platform 18 therebetween.

The airfoil 14 includes a leading edge 14a and a trailing edge 14b along which a generally concave pressure side joins a circumferentially opposite, generally convex suction side of the airfoil. Ambient air 20 flows downstream over the airfoil during operation and is pressurized thereby. Similar compressor blades may be found upstream and downstream of the exemplary blade illustrated for pressurizing the air in turn from stage to stage.

The rotor disk 12 may have any conventional form, such as being formed as a portion of a cylindrical spool having a locally enlarged ring in which a row of the blades are mounted during operation. In the exemplary embodiment illustrated in FIG. 1, a circumferentially extending dovetail slot 22 is formed in the perimeter of the disk 12 and is complementary to the dovetail 16 for radial retention thereof.

The dovetail 16 illustrated in FIG. 1 may have any conventional form such as a single pair of forward and aft lobes 24,26 disposed generally symmetrically about the radial or longitudinal centerline axis of the dovetail. The disk slot 22 is defined by a corresponding pair of forward and aft tangs 28,30 disposed outwardly of the corresponding lobes for radial retention thereof.

During operation, the disk 12 is rotated and centrifugal loads L are developed in the individual compressor blades. The centrifugal loads are carried through the corresponding dovetail 16 and effect corresponding reaction loads R in the disk tangs, which in turn are carried by the full hoop strength of the disk 12.

Since the airfoils 14 pressurize the air 20 during the operation, the individual airfoils 14 are also subject to aerodynamic loading represented, for example, by the counterclockwise bending moment M illustrated in FIG. 1. The bending moment is also reacted by the disk tangs, with the reaction forces R having corresponding, and typically different magnitudes at the forward and aft tangs.

Figure 2:
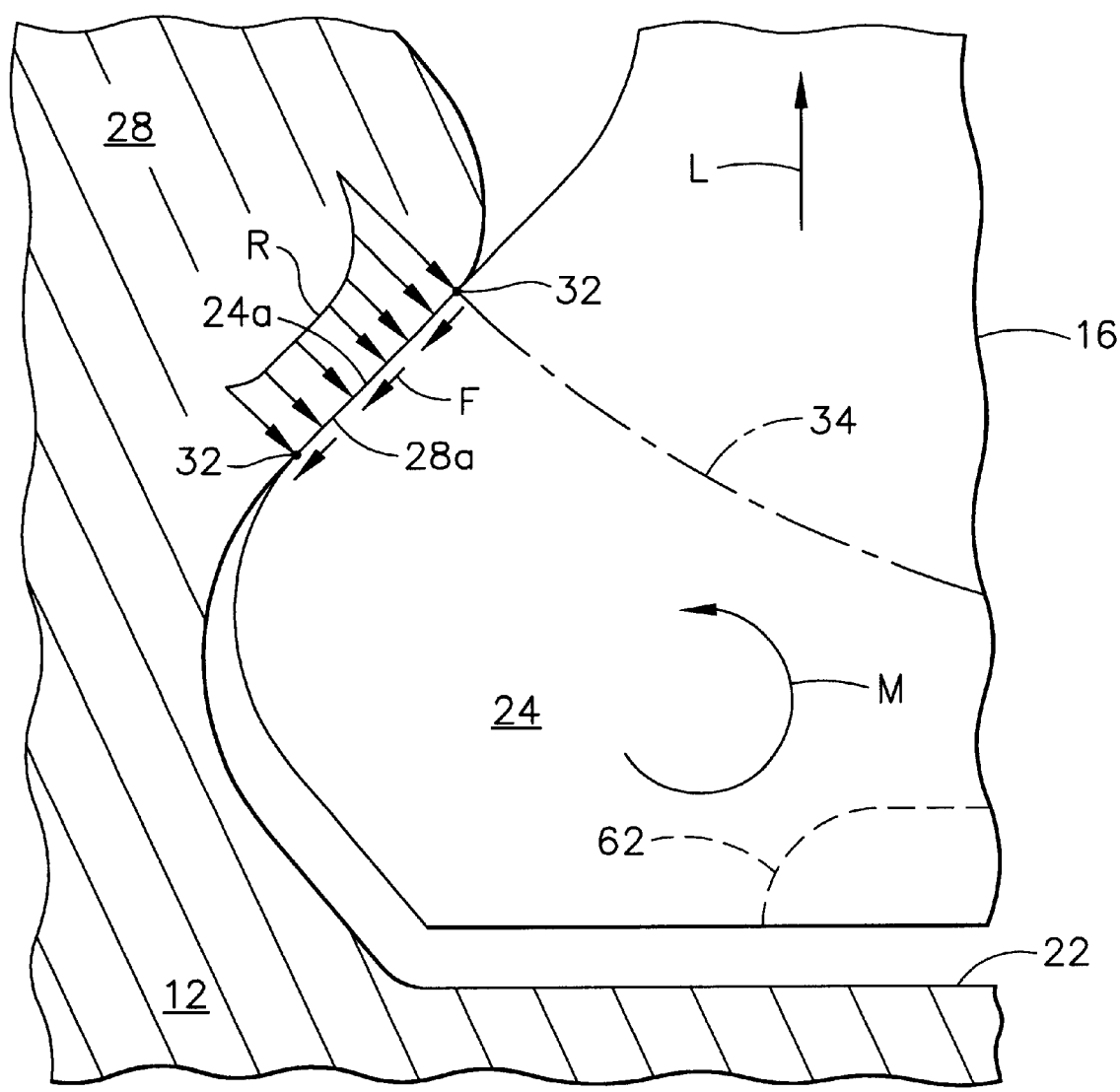
FIG. 2 is an enlarged, partly sectional view of the forward lobe of the dovetail illustrated in FIG. 1 engaging a corresponding forward tang of the rotor disk at corresponding pressure faces, with an exemplary reaction loading profile therebetween.

FIG. 2 illustrates in more particularity an exemplary loading profile between the forward lobe 24 and tang 28 as represented by the varying reaction forces labeled R. The forward lobe 24 has a radially outwardly facing contact or pressure face 24a which is generally straight in the axial direction and slightly curved in the circumferential direction to match the curvature of the rotor disk.

The lobe face 24a engages in contact during operation a corresponding, radially inwardly facing contact or pressure face 28a of the forward tang 28. The two pressure faces 24a,28a engage each other for most of the available length of the lobe and tang between a pair of opposite edges of contact 32. The aft lobe 26 and tang 30 illustrated in FIG. 1 are similarly configured like the forward lobe and tang illustrated in FIG. 2.

During operation, the centrifugal load L is carried in part through the forward lobe 24 to the forward tang 28, and in remaining part through the aft lobe and tang. The centrifugal load effects a nominal or average crush load between the outer and inner pressure faces, with a corresponding crush stress equal to the load divided by the effective contact area.

The aerodynamic loading represented by the bending moment M, for example, is also reacted through the corresponding disk tangs, and combines with the centrifugal load in the overall loading profile R between the lobes and tangs. Furthermore, the pressure faces are subject to relative displacement and friction during operation and develop a friction shear force F therealong which depends on the magnitude of normal reaction force on the pressure faces and a coefficient of friction therebetween. The loading profile is additionally affected by the temperature of operation of the blade disk.

As indicated above, the neck of minimum cross sectional area between the dovetail lobes typically experiences maximum stress during operation, with the neck being sized for reducing that stress to achieve infinite life of the dovetail in a preferred embodiment. During the initial cycles of a new compressor blade, the pressure faces are subject to relatively low amounts of friction, and maximum dovetail stress occurs at the neck thereof.

However, as cycles accumulate in the compressor blade to thousands of cycles representing high time operation, the frictional component of force at the pressure faces typically increases and has a pronounced affect on the resulting loading profile.

FIG. 2 illustrates schematically an exemplary reaction loading profile R subject to large friction which effects locally high reaction loading at the edges of contact 32. In particular, the outer edge of contact 32 on the forward lobe 24 experiences a maximum component of the reaction load resulting in a locally high stress thereat.

This high edge of contact stress can exceed the stress in the dovetail neck and can result in a crack initiation site for high time compressor blades operated at high stress. FIGS. 1 and 2 illustrate in phantom line an exemplary crack 34 which may propagate from the outer edge of contact 32 for high time blades exceeding a corresponding strength limit of the blade.

In order to improve dovetail design, such designs must be tested under suitable load cycles which may average 15,000 cycles for a compressor blade, which corresponds with about 45,000 hours of actual engine operation time. Such testing is impractical unless it is accomplished in a substantially shorter time achieving the high cycles.

As indicated above, conventional whirligig and component pull testing are ineffective for testing a dovetail design to include aerodynamic loading and frictional effects resulting in the loading profile having large local loads at the edges of contact.

Figure 3:
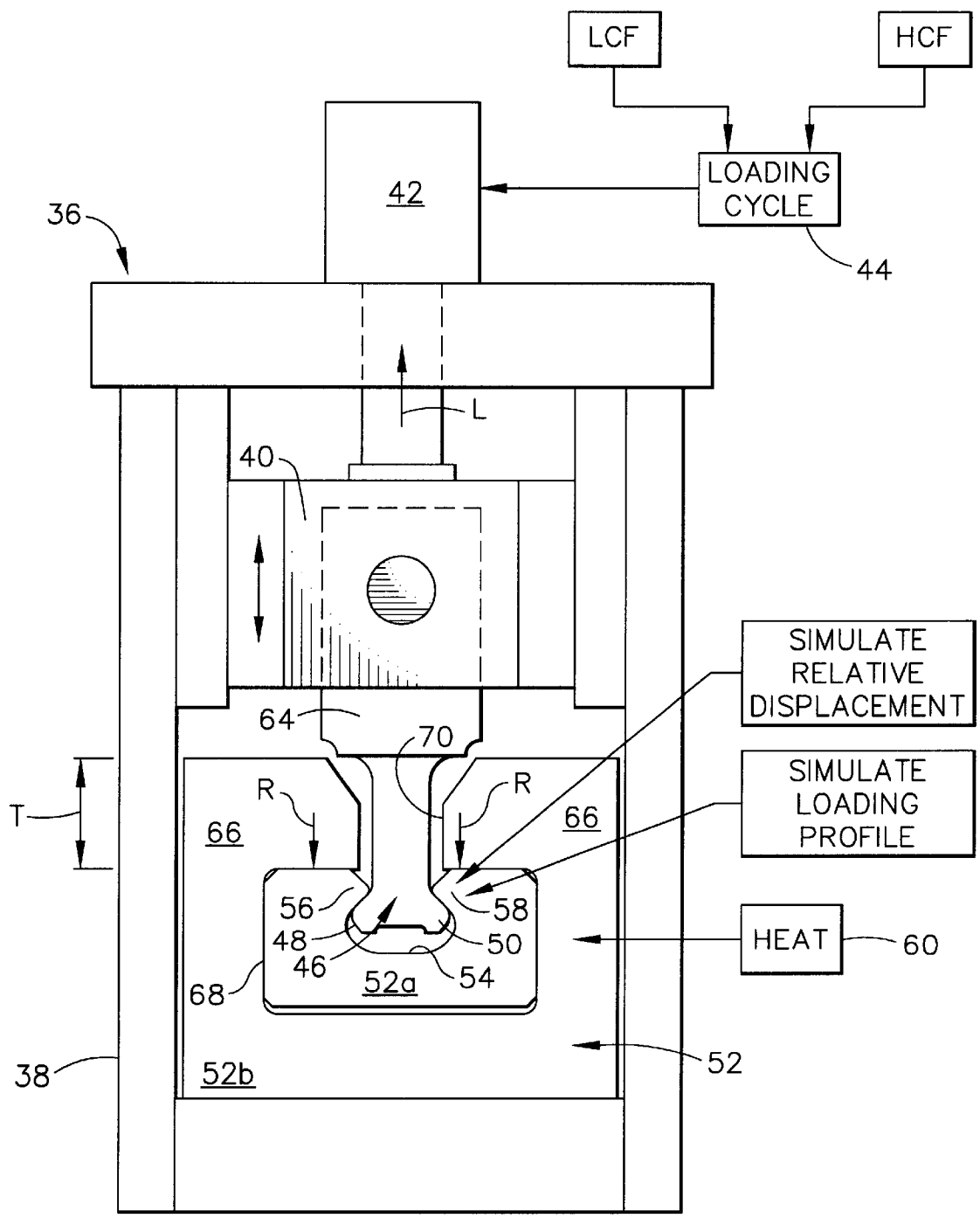
FIG. 3 is a partly schematic, elevational view of an apparatus for cycle testing a specimen dovetail in a cooperating fixture for simulating life of the blade dovetail illustrated in FIGS. 1 and 2 in accordance with an exemplary embodiment of the present invention.

Accordingly, FIG. 3 illustrates an improved endurance testing apparatus 36 for more accurately simulating dovetail loading in accordance with an exemplary embodiment of the present invention.

More specifically, the fatigue testing apparatus 36 may be modified from a conventional component pull testing apparatus and includes a frame 38, a chuck 40 mounted near the top thereof, a hydraulic actuator 42 operatively joined to the chuck, and an electrical controller 44 operatively joined to the actuator for controlling operation of the apparatus and the applied loading cycles therein. These features of the apparatus may have any conventional configuration and operation for longitudinally translating the chuck 40 for creating a nominal tension load L in a specimen dovetail 46 rigidly mounted in the chuck. The tension load L may be selected to correspond with the desired centrifugal load generated by the actual rotor blade 14 during operation, as well as other loads as desired.

The testing apparatus 36 illustrated in FIG. 3 is specifically configured for loading the specimen dovetail 46, which corresponds with the actual blade dovetail 16 illustrated in FIG. 1, for performing life testing thereof to eventual failure if desired. The specimen dovetail 46 shown in more particularity in FIG. 4 corresponds with a specific dovetail design, such as the actual dovetail 16 illustrated in FIG. 1.

Figure 4:
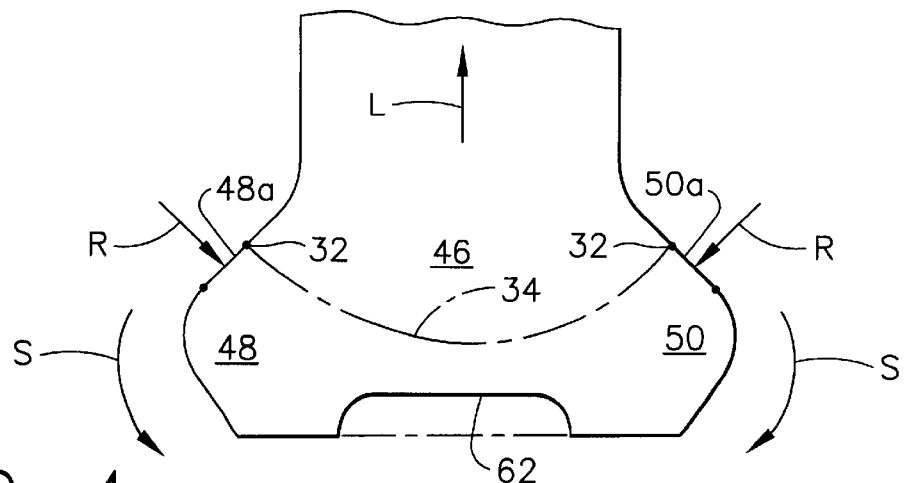
FIG. 4 is an enlarged elevational view of the specimen dovetail illustrated in FIG. 3 in an exemplary embodiment.

As shown in FIG. 4, the specimen dovetail 46 includes a single pair of lobes 48,50 matching in profile the respective forward and aft lobes 24,26 of the blade dovetail 16 being simulated. The forward and aft lobes 48,50 may have any suitable design for evaluation and directly corresponds with the actual size of the desired dovetail 16 for the intended rotor disk 12. Like the actual dovetail, the specimen dovetail includes radially outwardly facing pressure faces 48a,50a which match the corresponding pressure faces of the lobes 24,26.

As initially shown in FIG. 3, the testing apparatus also includes a specimen holding fixture 52 having a dovetail slot 54 defined by a pair of first and second tangs 56,58 which match in profile the respective disk tangs 28,30 of the rotor disk 12 illustrated in FIG. 1. The fixture tangs 56,58 have corresponding inner pressure faces, such as the forward pressure face 56a illustrated in more detail in FIG. 5, which match the corresponding pressure faces of the disk tangs 28,30.

In view of the relatively complex loading profile R illustrated in FIG. 2, the specimen dovetail 46 and holding fixture 52 illustrated in FIG. 3 are specifically configured for simulating that load profile when subjected to simple tension loading L effected by the actuator 42.

More specifically, the testing apparatus 36 additionally includes means for tailoring the relative stiffness of the specimen dovetail 46 and fixture 52 to simulate or match therebetween the desired loading profile R illustrated in FIG. 2 between the blade dovetail 16 and the rotor disk 12 at both pressure interfaces. By tailoring the relative stiffness, the particular geometry of the dovetail design may be more accurately evaluated by applying simulated centrifugal loading and aerodynamic loading, and at elevated temperature, if desired.

During testing, the specimen dovetail 46 is mounted in the fixture slot 54, with the former suitably held by the chuck 40, and the latter being fixedly joined to the bottom of the frame 38. The controller 44 may then be suitably programmed to effect a predetermined cycling load between the specimen dovetail and fixture for determining life of the specimen dovetail based on accumulated cycles thereof leading to eventual crack failure, if desired.

As shown schematically in FIG. 3, the apparatus may also include a suitable heater 60 effective for heating the specimen dovetail and fixture to elevated temperature experienced by an actual blade dovetail during operation. The controller 44 may be programmed for any desired loading cycle to simulate pure low cycle fatigue (LCF) or LCF with high cycle fatigue (HCF) interaction under temperatures up to about 500° F. as is accomplished in an otherwise conventional component pull test.

However, the dovetail specimen and fixture are specifically tailored in relative stiffness in accordance with the present invention for maintaining contact between the pressure faces and accurately reproducing the complex reaction loading profile therebetween, including the relatively high edge of contact loading occurring at high cycles.

The specimen and fixture may be tailored to simulate a predetermined loading profile including a nominal crush load due to centrifugal load, and edge of contact loads due to relative displacement and friction at corresponding edges of contact 32 of the pressure faces of the specimen lobes 48,50. As indicated above, crush stress is simply the components of the applied tension load L divided by the respective contact surface areas of the specimen lobes 48,50. By tailoring the relative stiffness of the specimen and fixture, the corresponding change in loading profile due to aerodynamic loading may be simulated, with relative displacement along the pressure faces and friction forces thereat following in turn.

More specifically, as the blade dovetail 16 illustrated in FIG. 1 is subject to centrifugal force and aerodynamic loading, the dovetail lobes and disk tangs are subject to elastic motion or displacement which is different at the forward and aft ends of the dovetail. Conventional 3D finite element analysis may be used to accurately predict the resulting loading profile, such as the profile labeled R in FIG. 2, between the blade dovetail and its supporting disk.

Figure 5:
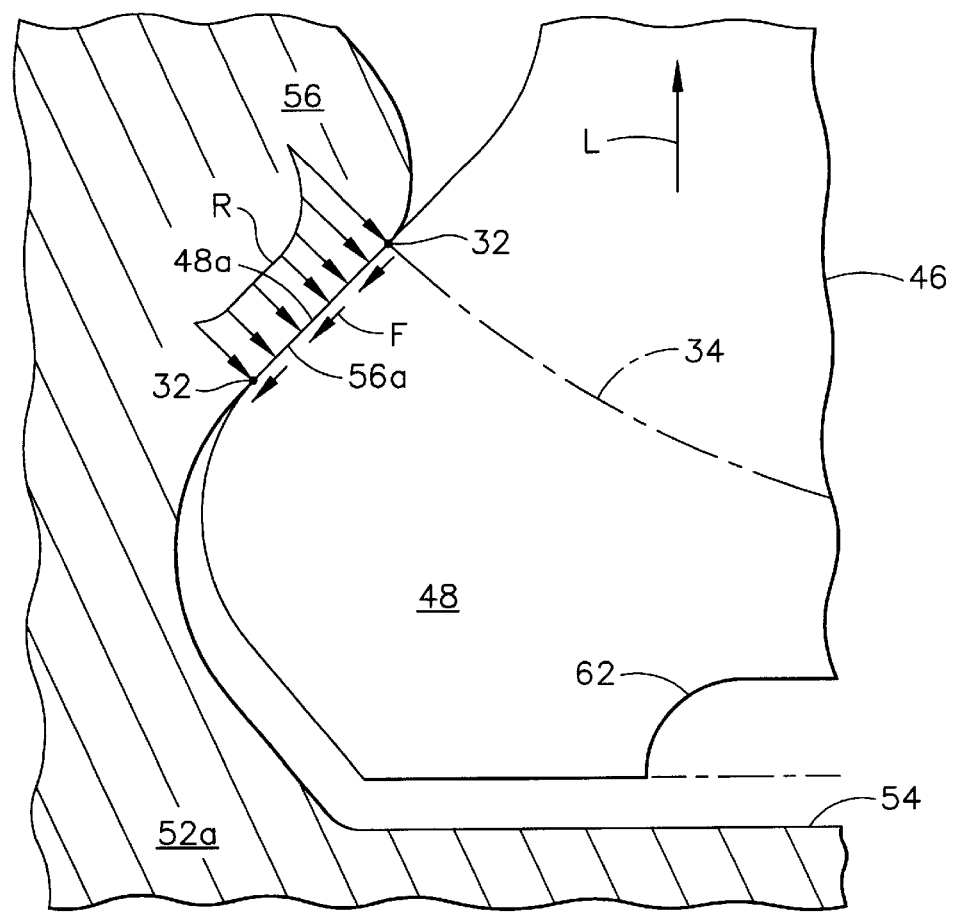
FIG. 5 is a partly sectional enlarged view of the specimen forward lobe, like FIG. 2, in accordance with an exemplary embodiment.

With the predetermined loading profile R, relative flexibility of the specimen dovetail and its fixture may be adjusted, by trial and error for example, for achieving substantially the same reaction loading profile R at the pressure faces of the specimen as illustrated schematically in FIG. 5. The relative stiffness may be determined using relatively simple two dimensional (2D) finite element analysis for analyzing the mechanics of deformation of the specimen dovetail and the supporting fixture.

In the preferred embodiment illustrated in FIGS. 4 and 5, the relative stiffness may be tailored by reducing the stiffness S of the specimen dovetail 46 axially between its opposite forward and aft lobes 48,50. For example, a suitable recess 62 may be centrally disposed between the two lobes 48,50 in the otherwise flat base or radially inner end of the dovetail.

As shown schematically in FIG. 4, the applied tension load L is directed upwardly, and nominal reaction loads R are directly downwardly on the two lobes 48,50. The two lobes are therefore subject to elastic bending, counterclockwise at the left and clockwise at the right. The two lobes have corresponding bending stiffness S of suitable magnitude for each lobe.

The tailored bending stiffness of the lobes ensures that the corresponding pressure faces thereof maintain in full contact with corresponding faces of the fixture, such as the forward pressure face 56a illustrated in FIG. 5. And, the corresponding flexibility of the specimen lobes may be used to effect a substantially accurate simulation of the desired loading profile R with locally high components at the edges of contact 32.

Comparing the actual blade dovetail 16 with its simulated counterpart specimen 46 illustrated in FIG. 4, shows that the two dovetails may be otherwise identical in profile and size except at the respective bases thereof. The specimen dovetail 46 illustrated in FIG. 4 includes the tailoring recess 62 which makes the specimen different in profile centrally between its lobes 48,50 as compared to the blade dovetail 16 illustrated in FIG. 1 which has a flat base between its two lobes 24,26. The recess 62 is illustrated in phantom in FIG. 1 to show the difference in profile, and the corresponding flat base is illustrated in phantom in FIG. 4 to additionally show the difference in the otherwise identical specimen and blade dovetails.

As initially shown in FIG. 3, the fixture 52 preferably includes at least an inner block 52a, and the tailoring means include the relatively rigid support of the two supporting tangs of 56,58 to prevent separation of the pressure faces between the dovetail lobes 48,50 and the tangs 56,58 for maintaining full pressure face contact as illustrated in FIG. 1 between the intended edges of contact 32.

Figure 6:
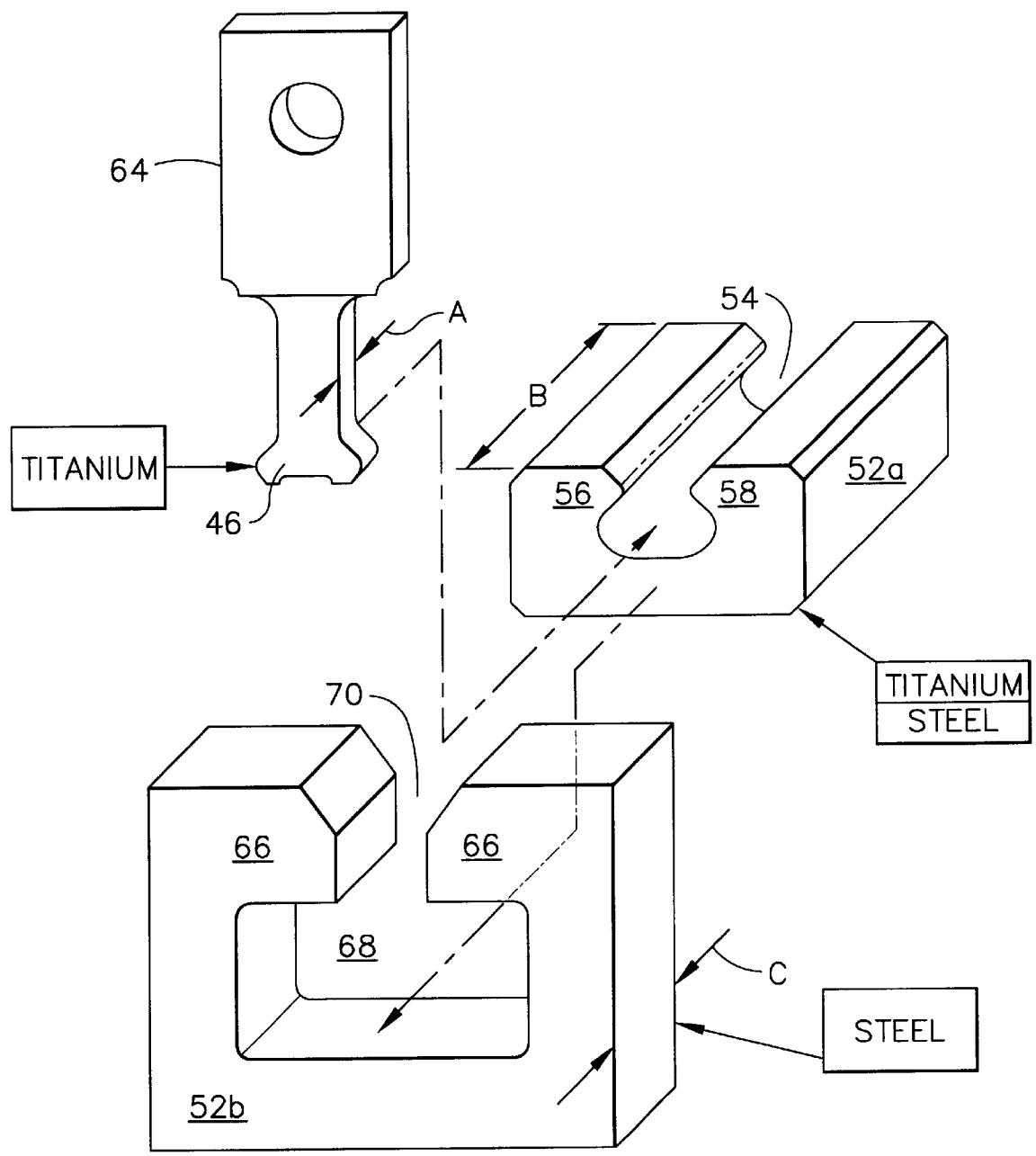
FIG. 6 is an exploded view of the specimen dovetail illustrated in FIG. 3 and cooperating supporting fixture including inner and outer blocks in accordance with an exemplary embodiment.

As shown in FIGS. 3 and 6, the fixture 52 preferably includes the inner block 52a with the dovetail slot 54 therein for receiving the specimen dovetail 46, and a complementary outer block 52b which supports or nests the inner block therein. Although the inner block 52a may be used alone without the outer block, and sized and configured with suitable stiffness relative to the specimen dovetail 46 for accurately reproducing the desired loading profile, it is preferably used in combination with the outer block 52b for further advantages.

More specifically, FIGS. 3 and 6 illustrate that the specimen dovetail 46 includes an integral mounting or supporting shank 64. The shank 64 includes an enlarged head with a central aperture therethrough which may be mounted in the chuck 40 with a corresponding pin extending through the aperture for rigidly securing the shank to the chuck 40 in a conventional manner used in component pull testing.

The outer block 52b includes a pair of integral J-shaped hooks 66 defining therebetween a central aperture or seat 68 for receiving and trapping the inner block therein. The outer profile of the inner block 52a is generally rectangular, and the seat 68 has a complementary rectangular profile in which the inner block is closely fit for support therein. The two hooks 66 are spaced apart from each other to define a slot or crevice 70 through which the shank 64 extends upwardly to the chuck.

As shown in FIG. 3, the outer block 52b may be suitably rigidly attached to the bottom of the frame 38 by corresponding bolts extending therebetween. Crevice 70 faces upwardly and is aligned with the fixture slot 54 so that the specimen dovetail 46 may be mounted in the slot 54, with the shank 64 extending upwardly through the crevice 70 to engage the chuck 40.

During testing, the actuator 42 lifts and loads the chuck 40 and the specimen 46 attached thereto. The specimen dovetail engages the tangs 56,58 of the inner block 52a which in turn are vertically trapped and retained by the hooks 66. A reaction load corresponding with the applied load L is carried through the outer block into the bottom of the frame placing the specimen and its shank nominally in tension as the load is applied. The load may then be cycled in varying amounts as desired for matching the desired LCF/HCF loading cycle experienced in a typical compressor operation.

The two fixture blocks illustrated in FIGS. 3 and 6 enjoy several advantages. For example, the inner block 52a may accurately include the fixture slot 54 in a small component. This component in turn may be mounted in a correspondingly larger outer block 52b which may be sized and configured for additionally tailoring the relative stiffness between the specimen dovetail and the fixture at its tangs 56,58.

For example, the hooks 66 as illustrated in FIG. 3 may have a vertical thickness T along the direction of applied loading specifically sized to rigidly support the underlying tangs 56,58, which in turn support the dovetail lobes 48,50 under the cycling load. In this way, relative flexibility may be effected in part and adjusted by controlling the dimensions of the outer block 52b, including in particular the thickness T of the supporting J-hooks 66.

As shown in FIG. 6, the inner block 52a, which includes the dovetail slot 54, may be made of the same material composition, such as titanium, as the specimen dovetail 46 to match the actual material composition of the blade dovetail 16 and rotor disk 12, which are typically titanium in a modern aircraft engine compressor. Since titanium is relatively expensive, a reduced amount thereof may be used in a correspondingly small inner block 52a.

Furthermore, the outer block 52b may have a different material composition than the inner block 52a, and may be formed of steel, for example. Steel is relatively less expensive than titanium and reduces costs when various configurations of the outer blocks 52b may be used in the testing program.

Additional costs may be saved by forming the inner block 52a of a different material than the specimen dovetail 46, such as using steel. Since the inner block 52a defines the immediate dovetail slot for supporting the specimen dovetail 46, its material composition may be secondary in importance when used in an accelerated cycling test. For each test of an individual specimen dovetail 46, however, it is desired to provide pristine material in the inner block 52a since wear and fretting thereof occurs over the duration of the cycle testing.

More specifically, the specimen dovetail 46 illustrated in FIG. 6 has a thickness A corresponding to the thickness of an actual blade dovetail. The inner block 52a has a length B along the slot 54 therein which is preferably longer or greater than the thickness A of the specimen dovetail. In this way, the specimen dovetail may be located at one position in the dovetail slot 54 for one test.

The inner block 52 may then be re-used in subsequent tests with a new specimen dovetail 46 mounted in the dovetail slot 54 at a different location having pristine material. For example, the length B of the inner block 52a may be slightly greater than about five times the thickness A of the specimen dovetail 46 so that the block may be used for five different tests.

The outer block 52b has a thickness C along the crevice 70 which is suitably larger than the thickness A of the specimen dovetail for suitably reacting the applied loads therethrough. The length B of the inner block 52a may therefore be also longer than the length C of the outer block 52b. The inner block may then be slid through the seat 68 to index the inner block for each test of a corresponding specimen dovetail.

In one exemplary dovetail design built and tested using the apparatus 36, a specimen dovetail was cycled to failure in about twenty-four hours to accurately reproduce an edge of contact fatigue failure resulting in separation along the crack 34 illustrated in FIG. 4 which corresponds with an analogous crack 34 in the corresponding actual dovetail 16 illustrated in FIG. 1. A comparable whirligig test would take several weeks to months to accumulate the same number of cycles, with the whirligig testing being ineffective for simulating the aerodynamic and frictional loads occurring in an actual compressor.

Although 3D finite element analysis may be used to accurately predict the loading profile between the pressure faces of a blade dovetail and its supporting disk, 2D finite element analysis is sufficient to accurately determine the required relative stiffness of the nested components. The 2D analysis can be used to design the geometry of the inner block 52a representing a disk specimen, the outer block 52b which holds and controls the stiffness of the supported inner block, and the desired tailoring of the specimen dovetail 46 for accurately producing a loading profile experienced in the three dimensional environment of the actual compressor blade.

The cooperation of the specimen dovetail and its supporting fixture accurately reproduces edge of contact loading experienced over accumulated cycles of dovetail life. The loads applied in the testing apparatus, LCF and HCF cycling thereof, and relative displacement along the pressure faces accurately reproduces those experienced in an actual compressor.

Accordingly, the design of the blade dovetail and its supporting rotor disk may be varied as desired and realistically tested in a short time for determining endurance life thereof. In this way, improvements in dovetail design may be made and evaluated in quick and efficient testing thereof.

Although the testing apparatus has been disclosed and configured for an exemplary circumferential-entry dovetail of a gas turbine engine compressor blade, it may also be used to advantage for other types of blade dovetails correspondingly simulated or modeled for experiencing corresponding loading profiles on the pressure faces thereof to accurately test endurance life.

Accordingly, what is desired to be secured by Letters Patent of the United States is the invention as defined and differentiated in the following claims in which we claim:

1. A method of simulating life of a blade dovetail mounted in a complementary slot in a rotor disk, comprising:

providing a specimen dovetail having a pair of lobes with pressure faces matching in profile respective lobes of said blade dovetail;

providing a fixture having a slot defined by a pair of tangs with pressure faces matching in profile respective tangs of said rotor disk;

tailoring relative stiffness of said specimen dovetail and fixture to simulate therebetween loading profile between said blade dovetail and rotor disk;

mounting said specimen dovetail in said fixture slot; and cycling load between said specimen dovetail and fixture for determining life of said specimen dovetail.

2. A method according to claim 1 wherein said loading profile includes crush load due to centrifugal load, and edge of contact loads at corresponding edges of said lobe pressure faces.

3. A method according to claim 2 wherein said relative stiffness is tailored to simulate relative displacement between said blade dovetail and rotor disk.

4. A method according to claim 3 wherein said relative stiffness is tailored by reducing stiffness of said specimen dovetail at said lobes thereof.

5. A method according to claim 4 wherein said specimen dovetail is different in profile between said lobes thereof than said blade dovetail.

6. A method according to claim 1 wherein said specimen dovetail is different in profile between said lobes thereof than said blade dovetail.

7. An apparatus for simulating life of a blade dovetail mounted in a complementary slot in a rotor disk, comprising:

a specimen dovetail having a pair of lobes with pressure faces matching in profile respective lobes of said blade dovetail;

a fixture having a slot defined by a pair of tangs with pressure faces matching in profile respective tangs of said rotor disk, with said specimen dovetail being mounted in said fixture slot;

means for tailoring relative stiffness of said specimen dovetail and fixture to simulate therebetween loading profile between said blade dovetail and rotor disk; and means for cycling load between said specimen dovetail and fixture for determining life of said specimen dovetail.

8. An apparatus according to claim 7 wherein said tailoring means are effective to simulate said loading profile including a crush load due to centrifugal load, and edge of contact loads at corresponding edges of said lobe pressure faces.

9. An apparatus according to claim 8 wherein said tailoring means are effective to simulate relative displacement between said blade dovetail and rotor disk.

10. An apparatus according to claim 7 wherein said tailoring means comprise a recess between said lobes of said specimen dovetail.

11. An apparatus according to claim 7 wherein said fixture comprises a block, and said tailoring means include rigid support of said tangs therein to prevent separation of said pressure faces at said lobes and tangs.

12. An apparatus according to claim 7 wherein:

said fixture comprises a block; and said tailoring means comprise a recess between said lobes of said specimen dovetail.

13. An apparatus according to claim 12 wherein said fixture further comprises an inner block including said tangs and slot receiving said specimen dovetail, and a complementary outer block supporting said inner block.

14. An apparatus according to claim 13 wherein:
said specimen dovetail includes an integral mounting shank; and
said outer block includes a pair of integral hooks defining therebetween a seat receiving said inner block, and spaced apart to define a crevice through which said shank extends.

15. An apparatus according to claim 14 wherein said tailoring means further comprise sizing said hook to rigidly support said tangs, and in turn support said lobes under said cycling load.

16. An apparatus according to claim 14 wherein said inner block along said slot therein is longer than said specimen dovetail is thick.

17. An apparatus according to claim 16 wherein said inner block along said slot therein is also longer than said outer block is thick.

18. An apparatus according to claim 14 wherein said inner block and specimen dovetail have the same material composition.

19. An apparatus according to claim 14 wherein said inner block and specimen dovetail have different material compositions.

20. An apparatus according to claim 14 wherein said inner block and outer block have different material composition.

* * * * *